United States Patent [19]
Pap et al.

[11] Patent Number: 4,950,682
[45] Date of Patent: Aug. 21, 1990

[54] ARTHROPODICIDAL COMPOSITIONS

[75] Inventors: László Pap; Péter Sárközi; Éva Somfai; András Szegő, all of Budapest; István Székely, Dunakeszi; György Hidasi, Budapest; Sándor Zoltán, Budapest; Anikó Deáknée Molnár, Budapest; Ágnes Hegedüs, Budapest; Béla Bertók, Budapest; Sándor Botár, Budapest; Antal Gajáry, Budapest; Lajos Nagy, Szentendre, all of Hungary

[73] Assignee: Chinoin Gyogyszer- es Vegyeszeti Termekek Gyara Rt., Budapest, Hungary

[21] Appl. No.: 307,395

[22] Filed: Feb. 6, 1989

[30] Foreign Application Priority Data

Feb. 5, 1988 [HU] Hungary ................. 540/88

[51] Int. Cl.$^5$ .................. A01N 43/38; A01N 43/30; A01N 53/00
[52] U.S. Cl. .................. 514/417; 514/531; 514/464
[58] Field of Search .................. 514/417, 531, 464

[56] References Cited

U.S. PATENT DOCUMENTS

| | | | |
|---|---|---|---|
| 3,067,091 | 12/1962 | Mahan et al. | 514/464 |
| 3,308,015 | 3/1967 | Harwood et al. | 514/464 |
| 3,906,089 | 9/1975 | Okuno et al. | 514/417 |
| 4,100,297 | 7/1978 | Grandadam et al. | 514/531 |
| 4,271,180 | 6/1981 | Yamaguchi et al. | 514/417 |
| 4,524,068 | 6/1985 | Szejtli et al. | 514/464 |
| 4,605,549 | 8/1986 | Carle | 514/531 |
| 4,845,126 | 7/1989 | Hidasi et al. | 514/521 |

FOREIGN PATENT DOCUMENTS 0005826 5/1979 European Pat. Off. .
2704066 8/1978 Fed. Rep. of Germany .
184614 10/1987 Hungary .

OTHER PUBLICATIONS

Miller, T. A., Salgado, V. L. The Mode of Action of Pyrethroids on Insects In: The Pyrethroid Insecticides, Ed. Lenoy, J. P. Taylor and Francis, pp. 43-97, London, 1985.

Primary Examiner—Douglas W. Robinson
Assistant Examiner—Kevin Weddington
Attorney, Agent, or Firm—Herbert Dubno; Jonathan Myers

[57] ABSTRACT

The present invention relates to synergistic arthropodicidal composition of several pyrethroidal active ingredients causing no damage to warm-blooded organisms comprising pyrethroides and piperonyl butoxide as active ingredient which comprises as pyrethroidal active ingredient 0.1–20% by weight of 1StransR-alpha-cyano-3-phenoxy-benzyl-3-(2,2-dichlorvinyl)-2,2-dimethyl-cyclopropane-cyrboxylate of the Formula I

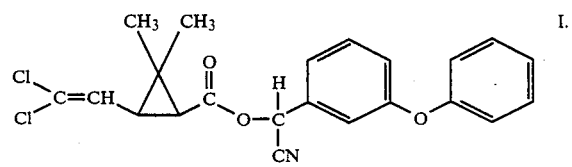

0.05–10% by weight of cis-trans-tetramethrin (3,4,5,6-tetrahydrophthalimido-methyl(1RS)-cis-trans-chrysantemate) or trans-tetramethrin of the Formula II

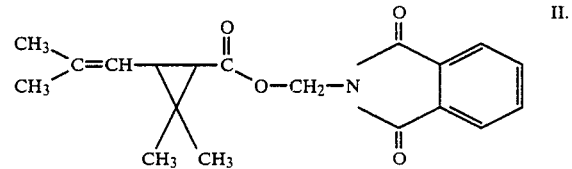

and a further pyrethroide, 0.1–40% by weight of piperonyl butoxide of the Formula III

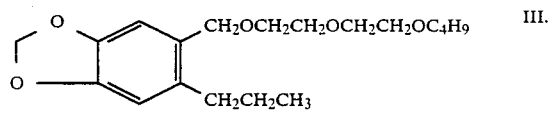

14 Claims, No Drawings

ARTHROPODICIDAL COMPOSITIONS

FIELD OF THE INVENTION

The present invention relates to arthropodicidal compositions containing several pyrethroidal active ingredients. The invention particularly relates to synergistic arthropodicidal compositions containing several pyrethroidal active ingredients which are not toxic to warm-blooded organisms.

DESCRIPTION OF THE INVENTION

The compositions contain as a pyrethroidal active ingredient 1StransR-alpha-cyano-3-phenoxy-benzyl-3-(2,2-dichlorvinyl)-2,2-dimethyl-cyclopropane carboxylate of the Formula I

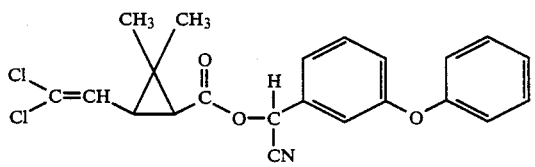

and tetramethrin or trans-tetramethrin of the Formula II

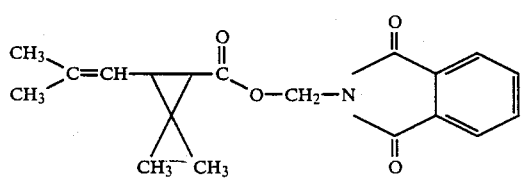

and optionally a further pyrethroidal substance as well as piperonyl butoxide of the Formula III and, optionally, additives.

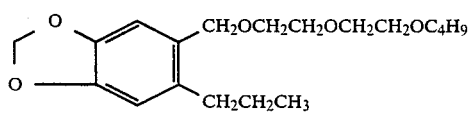

The compound of the Formula I amounts to 0.1–20% by weight and the compound of the Formula II to 0.05–10% by weight and the piperonyl butoxide of the Formula III amounts to 0.1–40% by weight. The remaining amount up to 100% consists of additives.

The following abbreviations are used throughout the specification:

Alphamethrin=(S)-alpha-cyano-3-phenoxybenzyl-(1R,3R)-3(2,2-dichlorvinyl)-2,2-dimethyl-cyclopropane-carboxylate and (R)-alpha-cyano-3-phenoxy-benzyl-(1S,3S)-3(2,2-dichlorvinyl)-2,2-dimethyl-cyclopropane carboxylate TET=tetramethrin=3,4,5,6-tetrahydro-phthalimido-methyl(1RS)-cis-trans-chrysanthemate deltamethrin=(S)-alpha-cyano-3-phenoxy-benzyl(1R,3R)-3-(2,2-dibrombinyl)-2,2-dimethyl-cyclopropane carboxylate trans TET=trans tetramethrin=3,4,5,6-tetrahydro-phthalimido-methyl(1RS)-trans chrysanthemate TRX=transmix=a mixture of 1StransR-alpha-cyano-3-phenoxy-benzyl-3-(2,2-dichlorvinyl)-2,2-dimethyl cyclopropane carboxylate and 1RtransS-alpha-cyano-3-phenoxy-benzyl-3-(2,2-dichlorvinyl)-2,2-dimethyl-cyclopropane carboxylate SF=synergistic factor PBO=piperonyl butoxide The composition according to the invention may be used in all those locations wherein only such substances may be applied which are substantially not toxic to warm-blooded organisms, such as agricultural and horticultural pests, i.e. pests occurring in the preserved food industry and refrigerating industry. Various parasitic arthropodal pests cause significant harm in stock breeding. By disquieting the animals the pests cause a reduction of their yield capacity, their gain in weight, they disturb their behavior and their technology tolerance, increasing thereby the number of compulsory slaughterings. Significant yield losses are caused by the storage arthropoda as well, and this is worsened by the fact that these crops are already produced (i.e. costs are already involved) and the protection is needed for the entire storing period during the utilization of the crops to avoid the presence of substances harmful to a man and animals.

During the protection against diseases propagated by various arthropoda such as malaria, yellow fever, sleeping fever, dysentery, plague, it is important that only such agents may be applied which are not toxic to warm-blooded organisms, are nontoxic dermally, and do not cause dermal irritation and allergy.

As the most widely used insecticides are neuroactive substances (nerve poison), the function of nerves is damaged in both lower and higher animals (F. Matsumura: Differential toxicities of insecticides and halogenated aromatics, Pergamon Press 1984). Consequently, the selectivity of most of the compositions is not sufficient.

The compositions according to the invention have an outstanding activity against the following pests: flies such as *Hydrotaea irritans, Morellia simples, M. Horitorum*, Haematobla spp., *Stomoxys calcitrans, Musca domestica, M. autumnalis*, Glossina app., Simulium spp., Culicoides, Phlebotomus spp., Tabanidae; fleas such as Xenopsylla spp., Pulex spp., Ctenocephalides app; bugs such as Cemex spp., Iriatoma spp., Rhodnius spp., Triatoma spp; lice such as Pediculus spp., *Phthirius pubis,* Damalinia, Haematophinus; ticks or mites such as Ixodes, Sporoptes spp., scabiei; mosquitoes such as Anopheles spp., Aedes spp., Culex spp., Mansonia spp.; cockroaches such as *Blattella germanica, Blatta orientalis, Periplaneta americana, Periplaneta australasie, Supella longipalpa;* various storage pests such as Iribolium spp., Trogoderma spp., Stegobium spp., Sitophilus spp., *Ienebrio spplk, Stagobium paniceum, Sitotroga cerealella, Zaorotes subfasciatus, Rhyzopertha dominica*, Ptinus spp., *Cryzaephilus surinamensis, O. mercator, Lasioderma serricorne*, Necrobia spp., dermestes spp., Carpopohilus spp., Dryptolestes spp., Mezium spp., *Alphitobius diapersinus, A.laevigatus*, Callosobruchus spp., Bruchus spp., *Anthrenus verbasci*, Ephestia spp., *Plodia interpunctella, Acaris siro, Tyrophagus putres, T. centiale, T. longinor, Tyrolichus casei* and; agricultural pests belonging to genera Lepidoptera, Coleoptera, Heteroptera, Homoptera, Hymenoptera, Diptera and Acariformes.

A preferred form of the composition according to the present invention contains as a further active ingredient 1RtransS-alpha-cyano-3-phenoxy-benzyl-3-(2,2-dichlorvinyl)-2,2-dimethyl-cyclopropane-carboxylate in an amount of 0.1–20% by weight. The ratio of 1StransR to 1RtransS amounts to 0.7-1.3:1.3-0.7, preferably 1:1.

We have now found that 1StransR isomer hitherto considered to be the least active of the 4 trans isomers of cypermethrin can be transformed to a synergistic active and stable composition when combined with tetramethrin and piperonyl butoxide. Thus the advantages of the very low toxicity against warm-blooded animals can be utilized and outstanding selective arthropodicidal composition may be prepared. The data relating to synergistic compositions are shown in Table 1.

TABLE 1

Interaction of transmix isomers and piperonyl butoxide on house fly (*Musca domestica*) tested by topical method

| isomers and active ingredient mixtures resp. | activity without PBO $LD_{50M}$ ng/fly | activity with PBO $(1:2)^x$ ng/fly | SF |
|---|---|---|---|
| 1RtransS | 5.78 | 4.58 | 1.26 |
| 1StransR | 571.50 | 278.62 | 2.05 |
| TRX | 6.70 | 3.76 | 1.78 |
| TRX + TET (10:1) | 8.02 | 2.97 | 2.70 |
| TRX + TET (10:5) | 8.41 | 2.87 | 2.93 | x = calculated to trans cypermethrins

As excipients anionic tensides, such as calcium alkyl aryl sulfonate, calcium dodecyl benzene sulfonate or non-ionic surfactants such as nonyl or dinonyl phenol ethoxylates (EO=16-20) are used. The composition may contain further non-ionic components such as tristyryl phenol ethoxylates (ED=20) etc.

As a filling agent the composition may contain solvents such as xylene, aromatic solvent mixture, aliphatic hydrocarbon mixtures, alkyl benzene, mineral or vegetable oil and solid carriers.

The formulation of the composition depends on the method of application.

In order to prepare emulsifiable compositions anionic tensides, non-ionic surfactants and other non-ionic components and solvents are preferable admixed to the mixture. As anionic tensides 2 to 5% by weight of calcium alkyl aryl sulfonate, and as non-ionic surfactant 1 to 2% by weight of nonyldinonyl phenol ethoxylates (EO=16-20) and as further non-ionic components 0.5-2% by weight of tristyryl phenol ethoxylates (EO=20) and as the solvent xylene may preferably be used.

A transparent emulsifiable composition may be prepared by using as anionic tenside 2.5-9% by weight of a calcium salt of alkyl aryl sulfonate, and as non-ionic surfactant 1.25-3.5% by weight of nonly-, dinonyl phenol ethoxylates (EO=16-20) and as further non-ionic component 0.7-3.5% by weight of tri-styryl phenol ethoxylates (EO=20) and as solvent preferably 5-10% by weight of xylene, 1-3% by weight of ethylene glycol and water up to 100% by weight.

Wettable powders can also be prepared by adding dispersing agents and carriers. According to a preferred feature as dispersing agent 1-2% by weight of dioctyl sulfosuccinate and 6-8% by weight of polymerized sodium naphthalene sulfonate and as carrier silicic acid and talc may be used.

Pests to be found at the waterside or in large fields, such as mosquitoes, can be combatted by using the composition according to the invention in ULV form by aeroplane or helicopter spraying. Such compositions contain apart from the active ingredient an aliphatic hydrocarbon mixture and mineral or vegetable oil at a ratio of 1:100-1:2 as filling agent. The composition of the invention can be formulated according to other methods as well, such as Hungarian Patent Applications Nos. 3245-87, 3246-87, 4975-87, 4974-87.

The active ingredients may be prepared by methods known per se such HU-PS 152 558 and EPA 86900 830 etc.

Known pyrethroidal combinations are e.g. mixtures of permethrin and decamethrin (EP No. 5826) and mixtures of permethrin and tetramethrin (HU-PS 184 614, DOS 2704 066). The compositions of the present invention are more efficient than the known compositions and are also active against certain strains which are resistant to said known compositions (See biological Example 3.).

SPECIFIC EXAMPLES

The details of the invention can be illustrated by the following non-limiting Examples.

I. Biological Examples

EXAMPLE 1

Test animal: In laboratory cultivated 3-5 day old female house fly (*Musca domestica*) WHO/SRS images. The active ingredient and n-butenol or ethoxy ethanol are dissolved in (cellosolve) and the solution is applied in 0.22 μl drops on the dorsal cuticule of the flies moderately narcotized with carbon dioxide. The treated flies are provided with sugar and water ad libitum in plastic glasses and evaluated after 24 hours. The ratio of killed flies is expressed in percentage (morality %). The $LD_{50}$ values are calculated from the obtained data by probit analysis.

The combinative interaction is given as a ratio of the expected activity (E) and the measured activity (M) calculated on the basis of the activity of the components per se. If the measured activity surpasses the expected activity then the activity is synergistic and if the activities are the same then the activity is additive, whereas if the measured activity does not achieve the expected activity then there is an antagonistic activity between the two components.

The expected value can be determined by harmonic average:

$$\text{Expected } LD_{50}(A+B) = \frac{A+B}{\frac{A}{LD_{50A}} + \frac{B}{LD_{50B}}}$$

The synergistic factor can be expressed as a ratio of the expected and measured values:

$$SF = \frac{\text{Expected } LD_{50}(A+B)}{\text{Measured } LD_{50}(A+B)}$$

wherein
  SF stands for synergistic factor,
  A and B stand for the amount of the components (or ratio thereof) and in the index they relate to the corresponding $LD_{50}$ values.

The obtained results show the outstanding synergistic activity of the 1:1 mixture of 1RtransS+1StransR (transmix) isomers compared to the different behavior of the various cypermethrin isomers (See Table 1).

In case of the piperonylbutoxide which itself is not very active the synergistic activity an be deduced from the decreasing number of the $LD_{50}$ values.

The effect of piperonyl butoxide on the activity of some cypermethrin isomers on the house fly (*Musca domestica*/SRS) measured by topical method is shown in the following table.

TABLE 2

| dose (ng × fly$^{-1}$) | activity per se | with PBO$^x$ | change of activity |
|---|---|---|---|
| 1RcisS | MORTALITY % | | |
| 0.50 | 5 | 5 | 0 |
| 0.72 | 15 | 20 | +5 |
| 1.03 | 30 | 30 | 0 |
| 1.47 | 50 | 65 | +15 |
| 2.10 | 80 | 75 | −5 |
| LD$_{50}$ | 1.37 | 1.30 | |
| 1RtransS | MORTALITY % | | |
| 1.56 | 10 | 10 | 0 |
| 2.59 | 20 | 30 | +10 |
| 4.32 | 40 | 50 | +10 |
| 7.20 | 60 | 65 | +5 |
| 12.00 | 75 | 85 | +10 |
| LD$_{50}$ | 5.78 | 4.58 | |
| 1StransR | MORTALITY % | | |
| 118 | 0 | 5 | +5 |
| 168 | 0 | 15 | +15 |
| 240 | 0 | 35 | +35 |
| 343 | 20 | 70 | +50 |
| 490 | 45 | 85 | +40 |
| 700 | 60 | 100 | +40 |
| 1000 | 80 | 100 | +20 |
| LD$_{50}$ | 571.5 | 278.6 | |
| 1RtransS+ 1StransR (1:1) | MORTALITY % | | |
| 1.56 | 0 | 15 | +15 |
| 2.59 | 10 | 30 | +20 |
| 4.32 | 30 | 55 | +25 |
| 7.20 | 50 | 80 | +30 |
| 12.00 | 80 | 95 | +15 |
| LD$_{50}$ | 6.70 | 3.76 | |

$^x$Ratio of pyrethroide and piperonyl butoxide = 1:2

EXAMPLE 2

Mixtures of transmix+tetramethrin of different ratio were tested by applying the above methods with piperonyl butoxide and without. The obtained results (Table 3) indicate a moderate antagonism in the case of simple combinations of two components: transmix and transmethrin. Table 4, however, shows an unexpected synergistic activity of the double combination admixed with piperonyl butoxide, which cannot be explained with any synergistic activity of the two pyrethroids per se and piperonyl butoxide. TET per se is ineffective at the used dose.

TABLE 3

Effect of mixtures of transmix and tetramethrin of various ratio on house fly (Musca domestica/SRS) measured by topical method

| dose (ng×fly$^{-1}$) TRX | TET | TRX | TET | TRX + TET measured activity | expected activity (%) | change of activity |
|---|---|---|---|---|---|---|
| TRX:TET = 10:1 MORTALITY % | | | | | | |
| 1.7 | 0.17 | 10 | 0 | 0 | 10 | −10 |
| 2.4 | 0.24 | 25 | 0 | 0 | 25 | −25 |
| 3.4 | 0.34 | 35 | 0 | 10 | 35 | −25 |
| 4.8 | 0.48 | 45 | 0 | 20 | 45 | −25 |
| 6.9 | 0.69 | 55 | 0 | 35 | 55 | −20 |
| 9.8 | 0.98 | 80 | 0 | 70 | 80 | −10 |
| LD$_{50}$ | | | | 5.16-8.49 | | |
| TRX:TET = 10:5 MORTALITY % | | | | | | |
| 1.7 | 0.82 | 10 | 0 | 0 | 10 | −10 |
| 2.4 | 1.18 | 25 | 0 | 0 | 25 | −25 |
| 3.4 | 1.68 | 35 | 0 | 10 | 35 | −25 |
| 4.8 | 2.40 | 45 | 0 | 25 | 45 | −20 |
| 6.9 | 3.43 | 55 | 0 | 35 | 55 | −20 |
| 9.8 | 4.90 | 80 | 0 | 65 | 80 | −15 |
| LD$_{50}$ | | | | 5.16-8.41 | | |

TABLE 4

Total effect of piperonyl butoxide, transmix and tetramethrin on house fly *Musca domestica*/SRS measured by topical method

| dose (ng × fly$^{-1}$) TRX | TET | TRX | TET | TRX + TET measured effect | expected effect (%) | change of effect |
|---|---|---|---|---|---|---|
| TRX:TET:PBO = 10:1:20 Mortality % | | | | | | |
| 1.7 | 0.17 | 10 | 0 | 15 | 10 | +5 |
| 2.4 | 0.24 | 25 | 0 | 35 | 25 | +10 |
| 3.4 | 0.34 | 35 | 0 | 60 | 35 | +25 |
| 4.8 | 0.34 | 45 | 0 | 80 | 45 | +35 |
| 6.9 | 0.69 | 55 | 0 | 95 | 55 | +40 |
| 9.8 | 0.98 | 80 | 0 | 100 | 80 | +20 |
| LD$_{50}$ | | | | 5.16-2.97 | | |
| TRX:TET:PBO = 10:5:20 Mortality % | | | | | | |
| 1.7 | 0.82 | 10 | 0 | 20 | 10 | +10 |
| 2.4 | 1.18 | 25 | 0 | 40 | 25 | +15 |
| 3.4 | 1.68 | 35 | 0 | 60 | 35 | +25 |
| 4.8 | 2.40 | 45 | 0 | 80 | 45 | +35 |
| 6.9 | 3.43 | 55 | 0 | 90 | 55 | +35 |
| 9.8 | 4.90 | 80 | 0 | 100 | 80 | +20 |
| LD$_{50}$ | | | | 5.16-3.0 | | |

EXAMPLE 3

Test of efficiency on resistant insects

House fly larvae (*Musca domestica*/NTR) collected from a pigfarm were bred to developed insects. The permethrin's activity was tested by enhanced increase of the LD$_{50}$ values, whereafter a great heterogenicity was observed, resulting in a levelling out of the dose-effect curve and in the enhanced increase of the LD$_{95}$. In order to strengthen resistance and to ensure the homogenicity of the population and an appropriate amount of test insects, the collected fly population was subjected to selection pressure for 5 generations at a level of LD$_{60}$, by treating 2000 male and 2000 female flies in each generation with the given dosage (LD$_{70}$) topically. The surviving flies gave the parent generation. The culturing was carried out by Sawicki as follows.

The insects were examined according to the method given in before Example 1. The LD$_{50}$ values were obtained by probit analysis.

TABLE 5

Efficiency of transmix: tetramethrin combinations on house fly (*Musca domestica*/NTR) tested by topical method

| active ingredients and mixtures | LD$_{50}$(ng×fly$^{-1}$) P$_0$ | F$_6$ | resistance factor LD$_{50F6}$/LD$_{50P0}$ |
|---|---|---|---|
| permethrin | 28.5 | 290.7 | 10.2 |
| tetramethrin | 450 | >5000 | >11 |
| TET + PBO (1:20) | 310 | 1500 | 5.2 |
| transmix | 8.6 | 17.5 | 2.2 |
| transmix + TET (10:1) | 9.5 | 21.2 | 2.2 |
| transmix + TET + PBO (10:1:20) | 5.8 | 7.2 | 1.2 |
| transmix + TET + PBO (10:1:40) | 5.3 | 7.1 | 1.3 |

TABLE 5-continued

Efficiency of transmix: tetramethrin combinations on house fly (Musca domestica/NTR) tested by topical method

| active ingredients and mixtures | $LD_{50}(ng \times fly^{-1})$ | | resistance factor $LD_{50F_6}/LD_{50P_0}$ |
|---|---|---|---|
| | $P_0$ | $F_6$ | |
| transmix + transTET + PBO (10:1:20) | 4.9 | 5.9 | 1.2 |

$P_0$ = parent generation
$F_6$ = offspring generation

The results indicate that the effect of transmix+tetramethrinpiperonyl butoxide mixtures on resistant flies is significant.

EXAMPLE 4

Emulsifiable concentrates prepared according to Examples 3 or 4 were diluted with 200-400-800-1600-3200-6400 fold water and the obtained emulsions were sprayed with a 2 layer pulverizer in 0.5 ml portions at a pressure of 2 bar into Petri-dishes of a diameter of 9 cm. After drying 3-5 days old female flies (*Musca domestica/* SRS) were placed to Petri-dishes (10 to each dish) in 4 replicates for each dosage. After 60 minutes the knocked down flies were calculated and their ratio was expressed in percent (see Table 6).

TABLE 6

| composition | dilution | | | | | |
|---|---|---|---|---|---|---|
| | 200 | 400 | 800 | 1600 | 3200 | 6400 |
| | knockdown (%) | | | | | |
| Emulsion of formulation Example 4 | 100 | 100 | 75 | 50 | 30 | 10 |
| Emulsion of formulation Example 3 | 100 | 100 | 85 | 60 | 35 | 10 |
| Stomosan ® | 100 | 80 | 40 | 15 | 0 | 0 |

Stomosan ® = Composition containing 200 g/l of commercially available permethrin The table shows that the knock-down effect is considerable even at a great dilution.

EXAMPLE 5

Test insects: cockroaches (*Blatella germanica*)

20 male cockroaches obtained from a 1-2 weeks continuous laboratory culture were treated topically in a mild carbon dioxide narcosis with 0.22 μl n-butanol solution of the test-compounds of a suitable concentration.

3 days after the treatment the insects, which were provided ad libitum with water and commercially available dogfood in plastic glasses, were evaluated. The ratio of the killed insects was expressed in percent. The results are shown in Table 7.

TABLE 7

| test components | dosage (ng×cockroach$^{-1}$) | | | | |
|---|---|---|---|---|---|
| | 4.5 | 9 | 18 | 39 | 78 |
| | Mortality (%) | | | | |
| TRX | 0 | 0 | 35 | 60 | 90 |
| TET | 0 | 0 | 0 | 0 | 0 |
| TET + PBO (1:20) | 0 | 0 | 0 | 0 | 0 |
| TRX + TET (10:1) | 0 | 5 | 30 | 60 | 90 |
| TRX + TET + PBO (10:1:20) | 15 | 55 | 85 | 100 | 100 |

EXAMPLE 6

Test insect: flour beetle (*Tribolium confusum*)

20 images obtained from a 1-2 weeks continuous laboratory culture were treated for each dosage with 0.22 μl of n-butanol solution of the tested compounds topically.

The treated insects were held in a glass vial sealed with a cotton wool stopper. The percent of the killed insects after 24 hours is shown in Table 8.

TABLE 8

| test compounds | dose (ng×insect$^{-1}$) | | | | | | | |
|---|---|---|---|---|---|---|---|---|
| | 0.78 | 1.56 | 3.13 | 6.25 | 12.5 | 25 | 50 | 100 |
| transmix (TRX) | 0 | 0 | 15 | 25 | 45 | 60 | 70 | 85 |
| tetramethrin (TET) | 0 | 0 | 0 | 0 | 0 | 0 | 0 | 0 |
| tetramethrin + PBO (1:20) | 0 | 0 | 0 | 0 | 0 | 0 | 0 | 0 |
| transmix + PBO (1:2) | 0 | 0 | 20 | 40 | 60 | 75 | 90 | 100 |
| TRX + TET + PBO (10:1:20) | 10 | 35 | 50 | 65 | 80 | 90 | 100 | 100 |

II Formulation Examples

EMULSIFIABLE CONCENTRATES (EXAMPLES 1-8)

Piperonyl butoxide, calcium salt of alkyl aryl sulfonate, nonyl phenol- and dinonyl phenol ethoxylate and tristyryl phenol ethoxylate are dissolved in 500 ml of xylene at 40° C. and the pyrethroides are added under stirring and the solution is completed to 1000 ml at 20° C. (See Table 9).

The compositions according to 1 to 8 in Table 9 were tested for stability in CIPAC A and D water at +30° C. in 0.2, 1 and 5 % by volume.

The samples were subjected to heat treatment for 14 days at 54°±2° C. and at the given temperature emulsion stability and redispersion tests were carried out in the above CIPAC waters. The 8 samples showed similar behavior within 10% standard deviation like the freshly prepared sample.

TABLE 9

| | Emulsifiable concentrates | | | | | | | |
|---|---|---|---|---|---|---|---|---|
| | amounts in g/l | | | | | | | |
| Example numbers | 1 | 2 | 3 | 4 | 5 | 6 | 7 | 8 |
| Transmix | 20 | 20 | 50 | 50 | 10 | 10 | 10 | 10 |
| Tetramethrin | 2 | 2 | 5 | 5 | 1 | 1 | 2 | 2 |
| PBO | 40 | 80 | 200 | 100 | 20 | 40 | 20 | 40 |
| Nonylphenolethoxylate (EO = 20) | 10 | 5 | 20 | 15 | 6 | 6 | 8 | 4 |
| Dinonylphenolethoxylate | 20 | 10 | 20 | 15 | 10 | 10 | 15 | 12 |

TABLE 9-continued

| | Emulsifiable concentrates amounts in g/l | | | | | | | |
|---|---|---|---|---|---|---|---|---|
| Example numbers | 1 | 2 | 3 | 4 | 5 | 6 | 7 | 8 |
| (EO = 16) Tristyrylphenolethoxylate | 10 | 15 | 20 | 5 | 10 | 5 | 8 | 8 |
| Ca salt of alkyl-aryl-sulfonate | 40 | 35 | 50 | 45 | 20 | 30 | 25 | 20 |
| Xylene | 1000 ml | 1000 ml | 1000 ml | 1000 ml | 1000 ml | 1000 ml | 1000 ml | 1000 ml |

TRANSPARENT SOLUTIONS

General Method

Piperonyl butoxide, calcium salt of alkyl aryl sulfonate, alkyl phenol ethoxylates and tristyryl phenol ethoxylate are dissolved in an aromatic solvent mixture of a suitable amount whereafter transmix and tetramethrin are added at 40° C. The obtained solution is poured into 500 ml of ion exchanged water containing 8% ethylene glycol and it is completed to 1000 ml at 20° C. with water containing 8% ethylene glycol (see Table 10, Examples 9-16).

TABLE 10

| | Transparent solutions amounts in g/l | | | | | | | |
|---|---|---|---|---|---|---|---|---|
| Example numbers | 9 | 10 | 11 | 12 | 13 | 14 | 15 | 16 |
| Transmix | 20 | 20 | 50 | 50 | 10 | 10 | 10 | 10 |
| Tetramethrin | 2 | 2 | 5 | 5 | 1 | 1 | 2 | 2 |
| PBO | 40 | 80 | 200 | 100 | 20 | 40 | 20 | 40 |
| Nonylphenolethoxylate (EO = 20) | 30 | 10 | 5 | — | 5 | 5 | — | — |
| Dinonylphenolethoxylate (EO = 16) | 5 | — | 10 | 15 | — | — | 15 | 10 |
| Tristyrylphenolethoxylate (EO = 20) | 20 | 30 | 45 | 55 | 80 | 60 | 55 | 45 |
| Ca salt of alkyl-aryl-sulfonate | 60 | 60 | 70 | 60 | 45 | 45 | 60 | 60 |
| Aromatic solvent mixture | 90 | 90 | 100 | 100 | 50 | 50 | 50 | 50 |
| 8% ethyleneglycol water solution | 1000 ml | 1000 ml | 1000 ml | 1000 ml | 1000 ml | 1000 ml | 1000 ml | 1000 ml |

The above transparent solutions were examined by the method described for the emulsifiable concentrates. The stability of the samples before and after the storage was found to be suitable.

EXAMPLE 17 (ULV)

20 g of piperonyl butoxide, 10 g of transmix and 1 g of tetramethrin were completely dissolved in 250 ml Solvesso 150 and it is completed to 1000 ml at 20° C. with paraffin oil.

EXAMPLE 18 (ULV)

10 g of piperonyl butoxide, 5 g of transmix and 1 g of tetramethrin are dissolved in 250 ml of Solvesso 150 whereafter it is completed with sunflower oil to 1000 ml at 20° C.

EXAMPLE 19 (WP)

In a two layer pulverizer laboratory fluidization drying equipment on 745 g of silicic acid at 40° C., under 2 bar liquid pressure and 3 bar air pressure a solution of 200 ml xylene, 100 g of piperonyl butoxide, 50 g of transmix and 5 g of tetramethrin is pulverized. To the dried powder 20 g of dioctyl sulfosuccinate and 80 g of polymerized sodium salt of alkyl naphthalene sulfonic acid are mixed. The homogeneous powder mixture is ground to a size below 20 micrometer by using an ultraplex mill. Moisturization time: 16 sec. Floatability according to CIPAC: 86%.

EXAMPLE 20

A solution of 150 ml of xylene, 20 g of piperonyl butoxide, 10 g of transmix and 1 g of tetramethrin is sprayed on 894 g of silicic acid according to Example 19. 15 g of dioctyl sulfosuccinate and 60 g of polymerized sodium alkyl naphthalene sulfonate are added to the dry powder mixture in a homogenizer, and the mixture is ground. Moisturization time of the powder mixture: 12 sec., floatability: 88%.

EXAMPLE 21

A solution of 75 ml of xylene, 2 g PBO, 1 g of transmix, and 0.1 g of tetramethrin is sprayed on 996 g of silicic acid by a method given in Example 19. The product can be used without grinding as a dusting agent.

EXAMPLE 22

A solution of 100 ml of xylene, 10 g of piperonyl butoxide, 5 g of transfix and 0.5 g of tetramethrin is applied to 985 g of silicic acid as given in Example 19. Dusting agent is obtained.

We claim:

1. A synergistic arthropodicidal composition ingredients causing no damage to warmblooded organisms which comprises a synergistic mixture of
   (1) as pyrethroid component the following active ingredients:
      (a) 0.1 to 20% by weight of 1StransR-alpha-cyano-3-phenoxy-benzyl-3-(2,2-dichlorovinyl)-2,2-dimethyl-cyclopropane carboxylate;
      (b) 0.1 to 20% by weight of 1RtransS-alpha-cyano-3-phenoxy-benzyl-3-(2,2-dichlorovinyl)-2,2-dimethyl-cyclopropane carboxylate, wherein the weight ratio of ingredient (a) to ingredient (b) is 0.7:1.3 to 1.3:0.7; and
      (c) 0.5 to 10% by weight of 3,4,5,6-tetra-hydro-phthalimido-methyl(1RS-cis-trans-chrysanthemate; or 3,4,5,6-tetrahydro-phthalimido-methyl (1RS)-trans-chrysanthemate; and (2) as a synergist component, 0.1 to 40% by weight of piperonyl butoxide.

2. The synergistic arthropodicidal composition defined in claim 1 wherein the weight ratio of ingredient (a) to ingredient (b) is 1:1 in the pyrethroid component.

3. The synergistic arthropodicidal composition defined in claim 1 wherein the weight ratio of ingredient (a) to ingredient (b) is 1:1 in the pyrethroid component, the weight ratio of ingredients (a) and (b) to ingredient (c) is 10:1 to 10:5 in the pyrethroid component, and the weight ratio of the ingredients (a) and (b) to ingredient (c) of said pyrethroid component and too the piperonyl butoxide forming said synergist component is 10:1:40 to 10:5:20.

4. The synergistic arthropodicidal composition defined in claim 3 wherein the weight ratio of the ingredients (a) and (b) to ingredient (c) of said pyrethroid component and to the piperonyl butoxide forming said synergist component is 10:1:20 to 10:5:20.

5. The synergistic arthropodicidal composition defined in claim 3 wherein the weight ratio of the ingredients (a) and (b) to ingredient (c) of said pyrethroid component and to the piperonyl butoxide forming said synergist component is 10:1:40 to 10:1:20.

6. A method of killing an arthropod while causing no damage to a warmblooded organism which comprises the step of applying to said arthropod or to the environment thereof, an insecticidally effective amount of the synergistic arthropodicidal composition defined in claim 1.

7. The method of killing an arthropod defined in claim 6 wherein the arthropod is a house fly, cockroach or flour beetle.

8. The composition according to claim 1 which comprises as additives 0.01–20% by weight of an anionic tenside, coloring agent, filling agent or a combination thereof in an amount to give 100% by weight.

9. The composition according to claim 8 which comprises 0.01–20% by weight of calcium dodecyl benzene sulfonate as anionic tenside, and which further comprises nonyl- or dinonyl-phenol ethoxylates (EO=1-6-20) as non-ionic surfactants and tristyryl phenol ethoxylate (EO=20) as a further non-ionic component.

10. The composition according to claim 8 which further comprises xylene, an aromatic solvent mixture, an aliphatic hydrocarbon mixture, alkyl benzene, or mineral or vegetable oil as a solvent.

11. The composition concentrate according to claim 8 which comprises 2 to 5% by weight of calcium alkyl aryl sulfonate as anionic tenside, and which further comprises 1–2% by weight of nonyl-, dinonyl phenol ethoxylate (EO=16–20) as a non-ionic surfactant and 0.5 to 2% by weight of tristyryl phenol ethoxylate (EO=20) as further non-ionic component and optionally xylene as a solvent.

12. A transparent emulsion composition as claimed in claim 8 which comprises 2.5 to 9% by weight of calcium alkyl aryl sulfonate as anionic tenside, and which further comprises 1.35–3.5% by weight of nonyl- or dinonyl-phenol ethoxylates as non-ionic surfactant (EO=16–20) and 0.7 to 3.5% by weight of tristyryl phenol ethoxylates as further non-ionic component (EO=20) and xylene, 1–3% by weight of ethylene glycol and water up to 100% by weight as a solvent.

13. A wettable powder composition as claimed in claim 8 which comprises 1 to 2% by weight of dioctyl sulfosuccinate and 6 to 8% by weight of polymerized sodium alkyl naphthalene sulfonate as dispersing agent with silicic acid and talc as carriers.

14. A ULV composition as claimed in claim 8 which comprises an aliphatic hydrocarbon mixture and mineral or vegetable oil at a ratio of 1:100–1:2 as filling agent.

* * * * *

UNITED STATES PATENT AND TRADEMARK OFFICE
CERTIFICATE OF CORRECTION

PATENT NO. : 4,950,682

DATED : 21 August 1990

INVENTOR(S) : Laszlo PAP et al

It is certified that error appears in the above-identified patent and that said Letters Patent is hereby corrected as shown below:

In the Abstract, line 13, for

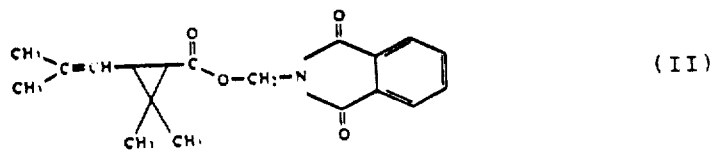 (II)

read

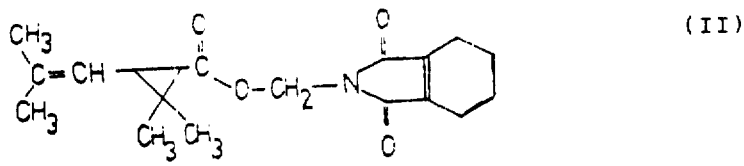 (II)

UNITED STATES PATENT AND TRADEMARK OFFICE
CERTIFICATE OF CORRECTION

PATENT NO. : 4,950,682

DATED : 21 August 1990

INVENTOR(S) : Laszlo PAP et al

It is certified that error appears in the above-identified patent and that said Letters Patent is hereby corrected as shown below:

In column 1, line 30, for

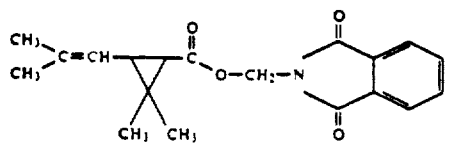

(II)

read

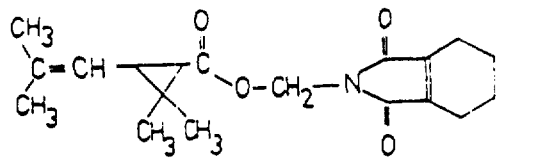

(II)

Signed and Sealed this

Second Day of March, 1993

Attest:

STEPHEN G. KUNIN

Attesting Officer

Acting Commissioner of Patents and Trademarks